United States Patent [19]

Davis

[11] 4,176,311
[45] Nov. 27, 1979

[54] POSITIVE ION SMOKE DETECTOR USING A TUNGSTEN WIRE PREHEATED IN HYDROGEN TO INCREASE SENSITIVITY

[75] Inventor: William D. Davis, Schenectady, N.Y.

[73] Assignee: General Electric Company, Schenectady, N.Y.

[21] Appl. No.: 753,774

[22] Filed: Dec. 23, 1976

[51] Int. Cl.² ............................................. G01N 27/62
[52] U.S. Cl. .................................. 324/468; 340/629; 313/230
[58] Field of Search .............. 324/33, 71 R; 340/237, 340/237 S, 628, 629; 73/25; 313/230; 250/423 R

[56] References Cited

U.S. PATENT DOCUMENTS

| | | | |
|---|---|---|---|
| 1,767,218 | 6/1930 | Kunsman | 313/230 |
| 2,157,478 | 5/1939 | Burkhardt | 313/230 |
| 2,550,498 | 4/1951 | Rice | 313/230 |
| 3,775,616 | 11/1973 | Tagashira et al. | 340/237 X |
| 3,823,372 | 10/1974 | Hanson et al. | 324/33 X |
| 3,932,851 | 1/1976 | Rayl et al. | 340/237 S |
| 4,047,101 | 9/1977 | Bauerle et al. | 324/33 |

OTHER PUBLICATIONS

White, W. C., Positive-Ion Emission a Neglected Phenomenon, Proc. of IRE, Aug. 1950, p. 852.

*Primary Examiner*—Robert J. Corcoran
*Attorney, Agent, or Firm*—Lawrence D. Cutter; Joseph T. Cohen; Marvin Snyder

[57] ABSTRACT

Smoke is detected by a surface ionization effect on a heated wire filament disposed opposite a negative ion collector electrode. Current flow between the wire and the electrode increases in the presence of smoke. The increase is probably attributable to surface ionization of smoke particles on the heated wire.

8 Claims, 2 Drawing Figures

POSITIVE ION SMOKE DETECTOR USING A TUNGSTEN WIRE PREHEATED IN HYDROGEN TO INCREASE SENSITIVITY

This invention relates to methods and apparatus for smoke detection. More specifically, this invention relates to methods and apparatus wherein thermal ionization on a hot surface (surface ionization) is used to detect smoke from combustion.

BACKGROUND OF THE INVENTION

Modern fire detection systems generally include smoke detecting elements. Prior art smoke detecting elements included ionization chambers containing a radioactive source, apparatus for measuring the attenuation of light, and apparatus for measuring resistance changes in thin film semiconductors. Light attenuation type smoke detectors are relatively complicated and, therefore, somewhat more expensive than thin film or ionization type detectors. The long term stability of thin film detectors remains unproven while the inclusion of radioactive sources may adversely affect the marketability of ionization chamber-type detectors.

Surface ionization on a hot filament in the presence of alkali metals has, in the prior art, been utilized for detection of halogen gases. Current flow between a heated filament and an adjacent cathode has been found to increase in the presence of a halogen-containing gas.

SUMMARY OF THE INVENTION

A heated metal wire, preferably tungsten or platinum, is disposed adjacent and maintained at a positive potential with respect to a collector electrode. Current flow between the wire and the electrode is found to increase markedly in the presence of smoke particles. The increase in current may be used to trigger an alarm or otherwise indicate the presence of smoke conditions. Two structures of the type described, one sealed and one opened to the ambient atmosphere, may be utilized in a bridge configuration to provide a highly stable, long lived smoke detector which requires only a fraction of a watt of power for operation and is suitable for long-lived operation from a line power supply.

It is therfore an object of this invention to provide inexpensive methods and apparatus for the detection of smoke.

Another object of this invention is to provide a low power, inexpensive reliable smoke detector which does not contain radioactive source material.

BRIEF DESCRIPTION OF THE DRAWINGS

The novel features characteristic of the present invention are set forth in the appended claims. The invention itself, together with further objects and advantages thereof, may best be understood by reference to the following detailed description taken in connection with the appended drawings in which:

DESCRIPTION OF THE PREFERRED EMBODIMENTS

Figure 1:
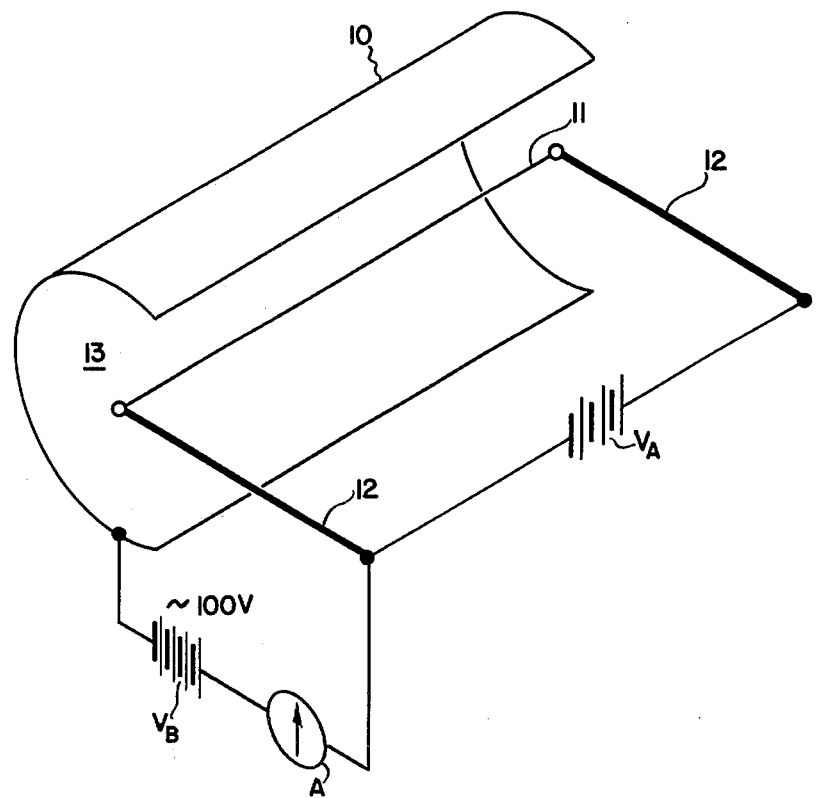
FIG. 1 is an apparatus for smoke detection in accordance with the present invention.

FIG. 1 is apparatus useful for the detection of smoke in accordance with the present invention. A wire 11, approximately 2.5 centimeters long, is mounted on support rods 12 and heated with current from a series connected power source $V_A$. A collector electrode 10 is disposed approximately 0.3 centimeters away from the wire 11 and is maintained at a negative potential with respect to the wire 11 by a voltage source $V_B$. By way of example, the voltage source $V_B$ may be a 100 volt line operated power supply. A current detector A, which may, for example, comprise an ammeter or a current-sensitive latching circuit is connected in series with the potential source $V_B$, the electrode 10, and the wire 11.

The wire 11 may comprise tungsten, platinum, nickel, rhenium, iridium, or nichrome. However, improved performance is obtained with tungsten and optimal performance with platinum wires. Optimal smoke detection is obtained with a wire 11 in the temperature range of approximately 500° C. to 700° C. The collector electrode 10 optimally comprises nickel sheet.

A sample of a test gas 13, which typically is the ambient atmosphere, which is to be tested for the evidence of smoke, is introduced into the space between filament 11 and the collector electrode 10. Current flow in the series circuit between the collector electrode and the filament is found to increase rapidly in the presence of smoke particles. It would appear that the increase of current with smoke is related to, but not identical to, the well-known increase in current which occurs in platinum filament, halogen leak detectors. However, the basic phenomenon responsible for the effect in these devices is not presently understood.

A test chamber utilized with the apparatus of the present invention comprises a closed box of 500 cubic centimeters volume. A burning string was introduced into the box for a time interval and then withdrawn. Calibration of the string using a light attenuation technique indicated approximately 0.1 percent light attenuation per foot of light path for each second of burning. Smoke levels employed for testing the detectors attenuated light in the range from 0.1 percent to 5 percent (1 to 50 second burning time).

A detector comprising a 0.0025 centimeter diameter tungsten wire at a temperature between 500° and 600° C. was tested in the apparatus described above. Both signal current (current in the presence of smoke) and background current (current in the absence of smoke) increased with filament temperature but the ratio of signal to background current remained substantially constant, above approximately 500° C. Tungsten wires which were fired in hydrogen at approximately 1000° C. prior to use provided maximum sensitivity in the smoke detector. Considerable variation in smoke detection sensitivity was experienced, probably due to variations in surface conditions on the tungsten wires. For approximately 0.1 percent smoke, the observed increase in detector current was typically a factor from approximately 10 to approximately 50. Higher smoke concentrations gave higher currents, but the increase was not linear. For example, one detector provided a background current of $1 \times 10^{-10}$ amps., a signal current of $5 \times 10^{-9}$ amperes at a 0.1 percent smoke level and a signal current of $1.3 \times 10^{-8}$ amperes for a 0.5 percent smoke level. For smoke levels above approximately 1 percent, the current decreased slightly.

A second smoke detector, comprising a 0.005 centimeter diameter platinum wire was tested in the manner indicated above. The behavior of the platinum wire detector was similar to the tungsten wire detector except that the response to smoke was roughly linear with concentration up to at least 3 percent. The output current in the presence of smoke increased with filament temperature to approximately 700 degrees and remained substantially constant at higher temperatures. After prolonged operation at high temperatures (approximately 1000° C.), the background current was found to decrease as did the sensitivity to smoke, however the signal to noise ratio remained approximately constant. For a fresh platinum wire at approximately 700° C., background current was approximately $1 \times 10^{-11}$ amperes; signal current at 1 percent smoke concentration was $2 \times 10^{-8}$ amperes. After prolonged heating at high temperature, background current decreased to $0.7 \times 10^{-12}$ amperes and the signal current at 1 percent smoke decreased to $2.5 \times 10^{-10}$ amperes.

Figure 2:
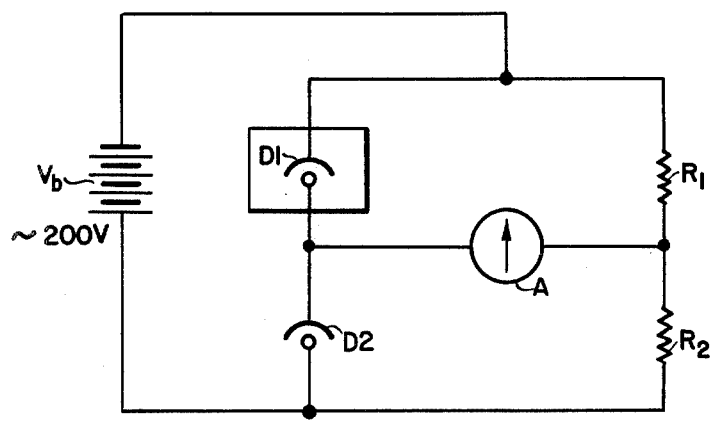
FIG. 2 illustrates two smoke detectors of the present invention operating in a bridge circuit configuration.

FIG. 2 is a bridge circuit for operating two smoke detecting elements of the present invention. Two identical smoke detecting elements, which may be the elements of FIG. 1, are connected in series across a potential source $V_B$. Suitable power supplies for heating the filaments are provided, but, to allow ease of description, are not shown in FIG. 2. A first detector D1 is sealed to exclude the entrance of smoke particles while the second detector D2 is open to allow entrance of the test gas. A resistive voltage divider comprising resistors R1 and R2 is connected in parallel with the series combination of the detecting elements D1 and D2. A current detecting source which may comprise an ammeter or a current sensitive latch circuit A is connected between the node of the detecting elements D1 and D2 and the node of the resistor divider at the junction of resistors R1 and R2. Thus, aging effects in the detectors D1 and D2 will tend to offset and maintain a balanced bridge circuit while a current increase in the detector D2, caused by smoke entering that detector, will unbalance the bridge and cause current to flow through the ammeter A. Any current decrease which may occur with aging of the detector elements is thus compensated.

Smoke detector elements of the present invention are relatively inexpensive and suitable for long-term line power operation. The presence of smoke produces a current increase of approximately 100 times which provides an adequate electric signal level to trigger an alarm circuit.

While the invention has been described in detail herein in accord with certain preferred embodiments thereof, many modifications and changes therein may be effected by those skilled in the art. Accordingly, it is intended by the appended claims to cover all such modifications and changes as fall within the true spirit and scope of the invention.

The invention claimed is:

1. A method for detecting smoke in an ambient atmosphere comprising:
   disposing a heated wire opposite a collector electrode, said heated wire comprising tungsten which has been fired in hydrogen gas;
   applying a negative electric potential on said electrode with respect to said wire;
   introducing a sample of a test gas between said wire and said electrode; and
   determining the presence of smoke particles in said test gas by an increase in electrical current flow between said wire and said electrode.

2. The method of claim 1 wherein said tungsten wire has been fired in hydrogen gas at a temperature of approximately 1000° C.

3. The method of claim 1 wherein the temperature of said wire is maintained between approximately 500° C. and approximately 700° C.

4. The method of claim 1 wherein the step of determining current flow between said wire and said electrode comprises:
   connecting two smoke detecting elements, each comprising a heated wire and a collector electrode, in a bridge circuit;
   sealing one of said detector elements to prevent the entrance of smoke; and
   introducing said test gas into said second detector, whereby the presence of said smoke in said second detector produces an unbalanced current in said bridge circuit.

5. An apparatus for detecting smoke in an ambient atmosphere comprising:
   a collector electrode;
   a heated tungsten wire disposed opposite said collector electrode, said heated wire having been fired in hydrogen gas;
   means for applying a negative electric potential on said electrode with respect to said wire; and
   detection means for determining the presence of smoke particles contained in said ambient atmosphere disposed between said wire and said electrode, said detection means operating by responding to a change in electrical current flow between said wire and said electrode.

6. The apparatus of claim 5 wherein said tungsten wire has been fired in hydrogen at a temperature of approximately 1,000° C.

7. The apparatus of claim 5 wherein the temperature of said wire is maintained between approximately 500° C. and approximately 700° C.

8. An apparatus for detecting smoke in an ambient atmosphere comprising:
   a first smoke detector element including a first heated tungsten wire disposed opposite a first collector electrode, said first electrode being maintained at a negative electric potential with respect to said first wire, said first wire comprising tungsten which has been fired in hydrogen gas;
   a second smoke detector element including a second heated tungsten wire disposed opposite a second collector electrode, said second electrode being maintained at a negative electric potential with respect to said second wire, said second wire comprising tungsten which has been fired in hydrogen gas, said second smoke detection element being disposed in a housing so as to seal said detection element from said ambient atmosphere; and
   a four-element bridge circuit detection means in which said first smoke detector element and said second smoke detector element are serially connected so as to form a two-element side of said bridge circuit so that the presence of smoke in said first detector produces an unbalanced current in said bridge circuit.

* * * * *